(12) United States Patent
Nishida et al.

(10) Patent No.: US 12,048,091 B2
(45) Date of Patent: Jul. 23, 2024

(54) STRETCHABLE WIRING BOARD AND DEVICE WITH ADHESIVE PATCH FOR LIVING BODY

(71) Applicant: Murata Manufacturing Co., Ltd., Nagaokakyo (JP)

(72) Inventors: Keisuke Nishida, Nagaokakyo (JP); Hayato Katsu, Nagaokakyo (JP); Yutaka Takeshima, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 227 days.

(21) Appl. No.: 17/839,775

(22) Filed: Jun. 14, 2022

(65) Prior Publication Data

US 2022/0312587 A1  Sep. 29, 2022

Related U.S. Application Data

(63) Continuation of application No. PCT/JP2021/040293, filed on Nov. 1, 2021.

(30) Foreign Application Priority Data

Nov. 25, 2020  (JP) ................. 2020-195163

(51) Int. Cl.
  *H05K 1/02* (2006.01)
  *A61B 5/00* (2006.01)

(52) U.S. Cl.
  CPC .......... *H05K 1/0283* (2013.01); *A61B 5/6833* (2013.01)

(58) Field of Classification Search
  CPC ............ A61B 2562/166; A61B 5/6833; H05K 1/0283; H05K 1/02; H05K 2201/09763;
  (Continued)

(56) References Cited

U.S. PATENT DOCUMENTS

2016/0219696 A1* 7/2016 Choi .................... H05K 1/0283
2017/0245362 A1* 8/2017 Iwase .................... H05K 1/095

FOREIGN PATENT DOCUMENTS

JP        2000353876 A    12/2000
JP        2016219543 A    12/2016
(Continued)

OTHER PUBLICATIONS

International Search Report in PCT/JP2021/040293, mailed Jan. 25, 2022, 2 pages.
(Continued)

*Primary Examiner* — Timothy J Thompson
*Assistant Examiner* — Guillermo J Egoavil
(74) *Attorney, Agent, or Firm* — ArentFox Schiff LLP (57) ABSTRACT

A stretchable wiring board that includes: a stretchable substrate; a first stretchable wiring extending in a length direction on a main surface side of the stretchable substrate; and a second stretchable wiring extending in the length direction on the main surface side of the stretchable substrate, the second stretchable wiring having a first portion with a first region overlapping on top of the first stretchable wiring on an end portion side of the first stretchable wiring, and a width of the first portion of the second stretchable wiring in a width direction orthogonal to the length direction is smaller than a width of the first stretchable wiring.

9 Claims, 2 Drawing Sheets

(58) Field of Classification Search
CPC ... H05K 2201/0311; H05K 2201/0323; H05K 2201/0329; H05K 2201/0373; H05K 2201/0391; H05K 2201/09263; H05K 2201/09272; H05K 2201/09736
USPC .................................................. 174/250, 254
See application file for complete search history.

(56) References Cited

FOREIGN PATENT DOCUMENTS

| | | |
|---|---|---|
| JP | 2017143257 A | 8/2017 |
| JP | 2017152687 A | 8/2017 |

OTHER PUBLICATIONS

Written Opinion in PCT/JP2021/040293, mailed Jan. 25, 2022, 4 pages.

\* cited by examiner

STRETCHABLE WIRING BOARD AND DEVICE WITH ADHESIVE PATCH FOR LIVING BODY

CROSS REFERENCE TO RELATED APPLICATIONS

The present application is a continuation of International application No. PCT/JP2021/040293, filed Nov. 1, 2021, which claims priority to Japanese Patent Application No. 2020-195163, filed Nov. 25, 2020, the entire contents of each of which are incorporated herein by reference.

FIELD OF THE INVENTION

The present invention relates to a stretchable wiring board and a device with an adhesive patch for living bodies.

BACKGROUND OF THE INVENTION

In recent years, a state and other information of a living body (for example, a human body) has been managed based on biological information acquisition and analysis using a wiring board.

In such a wiring board, two wirings may be provided so as to overlap with each other in part. When such two wirings are formed, for example, a conductive paste for one wiring is applied via a screen printing method, and then heat-treated to form the one wiring. Thereafter, the conductive paste for the other wiring is applied via a screen printing method to overlap on top of the one wiring on one end portion side thereof. However, pressing of a screen printing plate does not work sufficiently due to a step of the one wiring, and a printing bleeding may occur in which the conductive paste for the other wiring flows in a width direction, when the conductive paste for the other wiring is applied.

Patent Document 1 discloses a method for reducing printing bleedings in screen printing, in which two separate insulating layers on an insulating substrate are formed and a resistor ink is applied to fill between the two insulating layers so as to form a resistor whose width is regulated by the two insulating layers in a method for manufacturing a multilayer wiring board.

Patent Document 1: Japanese Patent Application Laid-Open No. 2000-353876

SUMMARY OF THE INVENTION

In the case of forming two wirings to overlap with each other in part during the manufacturing of a wiring substrate, if one wiring is formed between the two pre-formed insulating layers and then the conductive paste for the other wiring is applied using the method described in Patent Document 1, printing bleeding of the conductive paste for the other wiring can be suppressed by the two insulating layers.

However, in-plane rigidity of a region where the insulating layers are provided is increased when the insulating layers above are provided on the wiring board. When the wiring board is attached to a living body, the wiring board needs to have stretchability and is capable of following movements of the living body. But when the wiring board provided with the insulating layers above is stretched, stress would concentrate on the region provided with the insulating layers due to its high in-plane rigidity. Accordingly, as the wiring board stretches, the entire wiring does not uniformly stretch, leading to increases in a wiring resistance.

The present invention has been made to solve the above problems, and one object is to provide a stretchable wiring board capable of suppressing the impact of printing bleedings and the increases in wiring resistance during stretching. Further, another object of the present invention is to provide a device with an adhesive patch for living bodies having the stretchable wiring board.

A stretchable wiring board of the present invention includes: a stretchable substrate; a first stretchable wiring extending in a length direction on a main surface side of the stretchable substrate; and a second stretchable wiring extending in the length direction on the main surface side of the stretchable substrate, the second stretchable wiring having a first portion with a first region overlapping on top of the first stretchable wiring on an end portion side of the first stretchable wiring, and a width of the first portion of the second stretchable wiring in a width direction orthogonal to the length direction is smaller than a width of the first stretchable wiring.

A device with an adhesive patch for living bodies of the present invention includes the stretchable wiring board of the present invention.

The present invention can provide a stretchable wiring board which is capable of suppressing the impact of printing bleedings and the increases in wiring resistance during stretching. The present invention can further provide a device with an adhesive patch for living bodies having the stretchable wiring board above.

DETAILED DESCRIPTION OF THE INVENTION

The following describes a stretchable wiring board of the present invention. Note that the present invention is not limited to the following configuration, and may be appropriately modified without departing from the gist of the present invention. Further, the present invention may also include a combination of a plurality of preferred configurations in the following descriptions.

Figure 1:
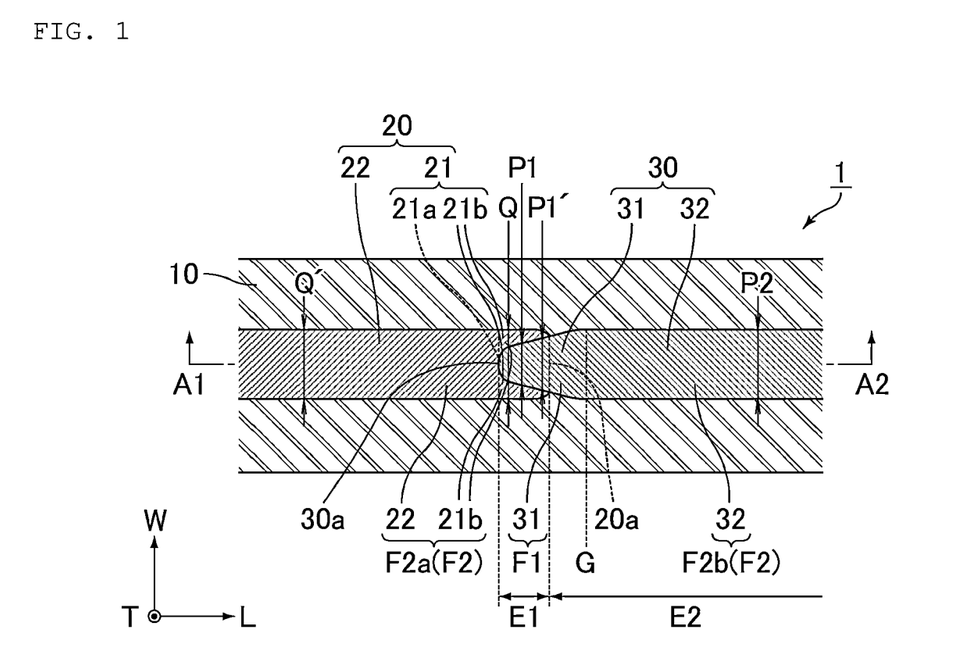
FIG. 1 is a schematic plan view in part illustrating an example of a stretchable wiring board of the present invention.
Figure 2:
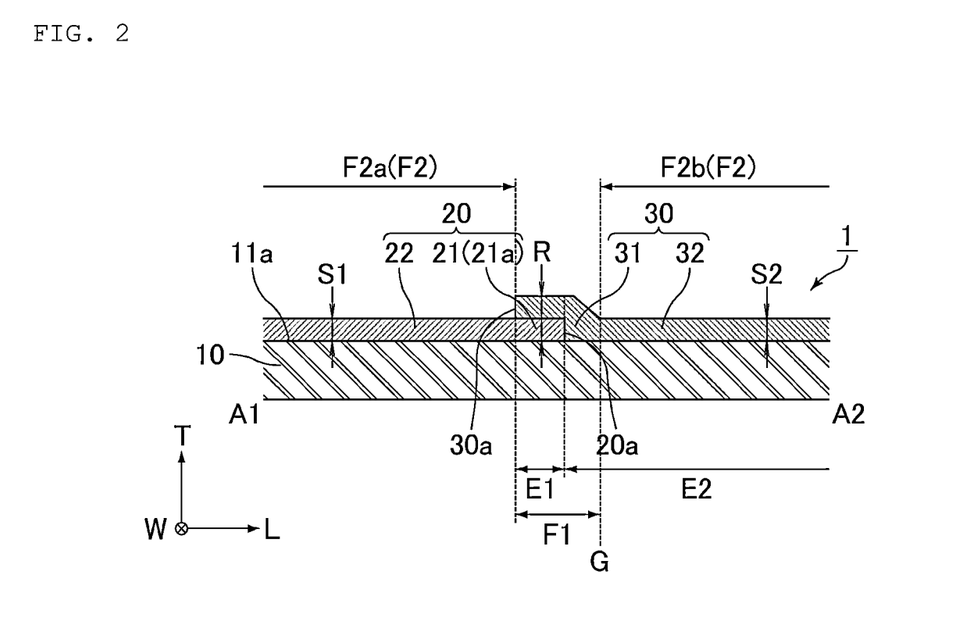
FIG. 2 is a schematic section view illustrating a portion corresponding to a line segment A1-A2 in FIG. 1.

FIG. 1 is a schematic plan view in part illustrating an example of the stretchable wiring board of the present invention. FIG. 2 is a schematic section view illustrating a portion corresponding to a line segment A1-A2 in FIG. 1.

According to FIGS. 1 and 2, a stretchable wiring board 1 includes a stretchable substrate 10, a first stretchable wiring 20, and a second stretchable wiring 30.

In the present description, a length direction, a thickness direction, and a width direction are respectively defined as L, T, and W, according to FIGS. 1 and 2. The length direction L, the thickness direction T, and the width direction W are orthogonal to each other. In FIGS. 1 and 2, the length direction L and the width direction W are along one main surface 11*a* of the stretchable substrate 10, and the thickness direction T is orthogonal to the one main surface 11*a* of the stretchable substrate 10.

In the present description, dimensions in the length direction, the thickness direction, and the width direction are respectively defined as a length, a thickness, and a width. Additionally, unless otherwise specified, the length, thickness, and width of each portion are illustrated as dimensions when the stretchable wiring board is not stretched. The length, thickness, and width of each portion are measured by viewing the stretchable wiring board in a plan view or a sectional view under an optical microscope. Additionally, the thickness of each portion may be measured with a contact film thickness gauge or a non-contact film thickness gauge.

The stretchable substrate 10 preferably includes at least one resin selected from the group consisting of a urethane resin, a silicone resin, an acrylic resin, and an olefin resin. Examples of the urethane resin include thermoplastic polyurethane (TPU).

When the stretchable wiring board 1 is attached to a living body, the thickness of the stretchable substrate 10 is preferably 100 μm or less, and more preferably 50 μm or less, so as not to inhibit the stretching of the surface of the living body. Further, the thickness of the stretchable substrate 10 is preferably 10 μm or more.

Figure 3:
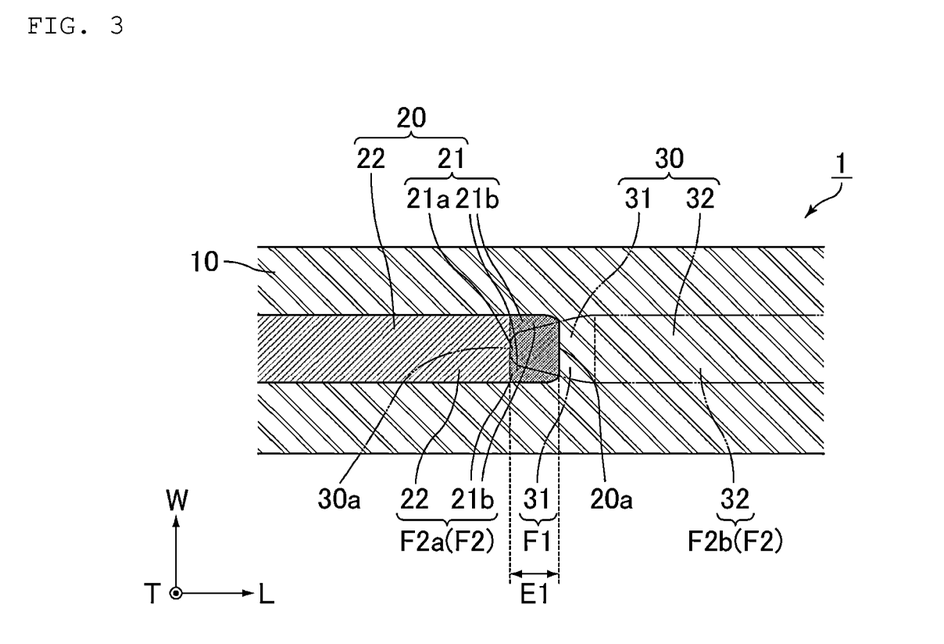
FIG. 3 is a schematic plan view for explaining a configuration of a first stretchable wiring in FIG. 1.

FIG. 3 is a schematic plan view for explaining a configuration of the first stretchable wiring in FIG. 1. FIG. 3 illustrates a state focusing on the first stretchable wiring 20 while showing the first stretchable wiring 20 and the second stretchable wiring 30 at the same time. The first stretchable wiring 20 is described below referring to FIG. 3 in addition to FIGS. 1 and 2.

The first stretchable wiring 20 extends in the length direction L on the one main surface 11a side of the stretchable substrate 10. More specifically, the first stretchable wiring 20 is provided on the one main surface 11a of the stretchable substrate 10 and extends in the length direction L.

The first stretchable wiring 20 overlaps under the second stretchable wiring 30 on one end portion 20a side thereof. More specifically, the first stretchable wiring 20 is sandwiched between the stretchable substrate 10 and the second stretchable wiring 30 in the thickness direction T on the one end portion 20a side. In such a state, the first stretchable wiring 20 and the second stretchable wiring 30 are connected.

The first stretchable wiring 20 includes a first portion 21 located on the one end portion 20a side in the length direction L, and a second portion 22 adjacent to the first portion 21.

As illustrated in FIG. 3, the first portion 21 of the first stretchable wiring 20 has a portion 21a overlapping with the second stretchable wiring 30 and a portion 21b not overlapping with the second stretchable wiring 30. More specifically, the first portion 21 of the first stretchable wiring 20 has the portion 21a overlapping with a first portion 31 of the second stretchable wiring 30 and the portion 21b not overlapping with the first portion 31 of the second stretchable wiring 30.

In the first portion 21 of the first stretchable wiring 20, the portion 21a overlapping with the second stretchable wiring 30 and the portion 21b not overlapping with the second stretchable wiring 30 have the same dimensions in the length direction L. In other words, in the first portion 21 of the first stretchable wiring 20, the portion 21a overlapping with the second stretchable wiring 30 and the portion 21b not overlapping with the second stretchable wiring 30 have the same dimension in the length direction L as a region E1 where the first stretchable wiring 20 and the second stretchable wiring 30 overlap.

Figure 4:
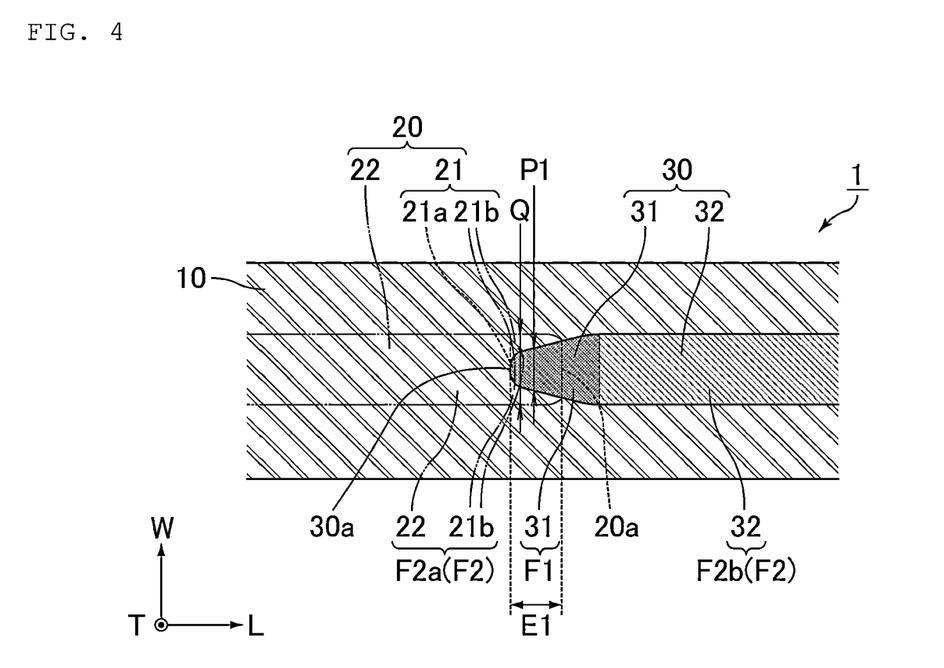
FIG. 4 is a schematic plan view for explaining a configuration of a second stretchable wiring in FIG. 1.

FIG. 4 is a schematic plan view for explaining a configuration of the second stretchable wiring in FIG. 1. FIG. 4 illustrates a state focusing on the second stretchable wiring 30 while showing the first stretchable wiring 20 and the second stretchable wiring 30 at the same time. The second stretchable wiring 30 is described below referring to FIG. 4 in addition to FIGS. 1 and 2.

The second stretchable wiring 30 extends in the length direction L on the one main surface 11a side of the stretchable substrate 10. More specifically, the second stretchable wiring 30 is provided on the one main surface 11a of the stretchable substrate 10 except one part and extends in the length direction L.

The second stretchable wiring 30 overlaps on top of the first stretchable wiring 20 on one end portion 30a side thereof. More specifically, the first stretchable wiring 20 is sandwiched between the second stretchable wiring 30 on the one end portion 30a side and the stretchable substrate 10 in the thickness direction T.

It can be seen from a plan view of the stretchable wiring board 1 under an optical microscope that the second stretchable wiring 30 overlaps on top of the first stretchable wiring 20 on the one end portion 30a side.

The second stretchable wiring 30 has a first portion 31 located on the one end portion 30a side.

The first portion 31 of the second stretchable wiring 30 has at least a region E1 where the first stretchable wiring 20 and the second stretchable wiring 30 overlap. A width P1 of the first portion 31 of the second stretchable wiring 30 is smaller than a width Q of the first stretchable wiring 20.

When the second stretchable wiring is formed so as to overlap on top of the first stretchable wiring on one end portion side in conventional methods for manufacturing stretchable wiring boards, for example, a conductive paste for the first stretchable wiring is applied in the length direction on one main surface of the stretchable substrate via a screen printing method, and then heat-treated to form the first stretchable wiring. Subsequently, the conductive paste for the second stretchable wiring is applied in the length direction on the one main surface of the stretchable substrate via a screen printing method, so as to overlap on top of the first stretchable wiring on one end portion side. During this process, since a step is formed due to the first stretchable wiring in the length direction, a screen printing plate and the stretchable substrate are difficult to keep in close contact with each other in a region near the step, leading to printing bleedings of the conductive paste for the second stretchable wiring. In addition, since the step due to the first stretchable wiring is also formed in the width direction, both the steps in the length direction and in the width direction would cause the printing bleedings of the conductive paste for the second stretchable wiring if the conductive paste for the second stretchable wiring is shifted in the width direction. When the printing bleedings of the conductive paste for the second stretchable wiring occur, the width of the second stretchable wiring to be formed tends to increase in a region overlapping with the first stretchable wiring, possibly resulting in a contact with other surrounding stretchable wirings which further causes a short-circuit.

On the other hand, in the stretchable wiring board 1, the width P1 of the first portion 31 of the second stretchable wiring 30 is smaller than a width Q of the first stretchable wiring 20. In other words, when the second stretchable wiring 30 is formed for manufacturing the stretchable wiring board 1, the width P1 of the first portion 31 of the second stretchable wiring 30 which is easily affected by the printing bleedings is still smaller than the width Q of the first stretchable wiring 20, regardless of whether printing bleedings of the conductive paste for the second stretchable wiring 30 occur due to the step of the first stretchable wiring 20. Accordingly, the impact of printing bleedings can be said to be reduced in the stretchable wiring board 1.

In a conventional stretchable wiring board, in-plane rigidity in a region where two stretchable wirings overlap tends to be higher than that in other regions where two stretchable wirings do not overlap. On the other hand, in the stretchable wiring board 1, since the width P1 of the first portion 31 of the second stretchable wiring 30, which is at least present in the entire region E1, is smaller than the width Q of the first stretchable wiring 20, an increase in in-plane rigidity of the region E1 can be suppressed. In this way, concentration of stress in the region E1 during stretching can be reduced, so that the increases in resistance of the first stretchable wiring 20 and the second stretchable wiring 30 can also be reduced in the stretchable wiring board 1.

As described above, at least the region E1 is included in the first portion 31 of the second stretchable wiring 30 and the width P1 thereof is smaller than the width Q of the first stretchable wiring 20. The width P1 of the first portion 31 of the second stretchable wiring 30 may be determined at various positions in the first portion 31 of the second stretchable wiring 30. Among them as illustrated in FIG. 1, a width P1' determined at the center position in the length direction L in the first portion 31 of the second stretchable wiring 30 is certainly smaller than the width Q of the first stretchable wiring 20. The difference between the width P1' determined at the center position in the length direction L in the first portion 31 of the second stretchable wiring 30 and the width Q of the first stretchable wiring 20 is preferably 30 μm or more, and more preferably 50 μm or more. Additionally, to increase durability of the first portion 31 of the second stretchable wiring 30, the difference between the width P1' determined at the center position in the length direction L in the first portion 31 of the second stretchable wiring 30 and the width Q of the first stretchable wiring 20 is preferably half or less of the width Q of the first stretchable wiring 20.

The width Q of the first stretchable wiring 20 is determined according to the minimum width of the first stretchable wiring 20. As illustrated in FIG. 1, the width Q of the first stretchable wiring 20 is preferably determined according to the first portion 21 of the first stretchable wiring 20. On the other hand, as illustrated in FIG. 1, when the width of the first stretchable wiring 20 can be regarded as being substantially constant over the first portion 21 and the second portion 22, a width Q' of the first stretchable wiring 20 determined at a position 2 mm away from the boundary between the first portion 21 and the second portion 22 of the first stretchable wiring 20 toward the second portion 22 side may be representatively determined as the width Q of the first stretchable wiring 20.

As illustrated in FIGS. 1 and 2, the first portion 31 of the second stretchable wiring 30 is preferably across the region E1 where the first stretchable wiring 20 and the second stretchable wiring 30 overlap and a region E2 where the first stretchable wiring 20 and the second stretchable wiring 30 do not overlap. In this case, the impact of printing bleedings can be said to be reduced in a wide range over the region E1 to the region E2. Additionally, the length of the portion in the region E2 in the first portion 31 of the second stretchable wiring 30 is preferably 100 μm to 300 μm.

Further, the first portion 31 of the second stretchable wiring 30 may exist only in the region E1.

The second stretchable wiring 30 preferably includes the first portion 31 in the length direction L, and a second portion 32 adjacent to the first portion 31, as illustrated in FIGS. 1 and 2. In this case, a width P2 of the second portion 32 of the second stretchable wiring 30 is preferably larger than the width P1 of the first portion 31 of the second stretchable wiring 30.

It is natural that the width P1' determined at the center position in the length direction L in the first portion 31 of the second stretchable wiring 30 is preferably smaller than the width P2 of the second portion 32 of the second stretchable wiring 30, but the difference between the width P1' determined at the center position in the length direction L in the first portion 31 of the second stretchable wiring 30 and the width P2 of the second portion 32 of the second stretchable wiring 30 is preferably 30 μm or more, and more preferably 50 μm or more. Additionally, to increase durability of the first portion 31 of the second stretchable wiring 30, the difference between the width P1' determined at the center position in the length direction L in the first portion 31 of the second stretchable wiring 30 and the width P2 of the second portion 32 of the second stretchable wiring 30 is preferably half or less of the width P2 of the second portion 32 of the second stretchable wiring 30.

The width P2 of the second portion 32 of the second stretchable wiring 30 is preferably the same as, or may be different from, the width Q of the first stretchable wiring 20.

The width P2 of the second portion 32 of the second stretchable wiring 30 is determined according to the minimum width of the second portion 32 of the second stretchable wiring 30. On the other hand, as illustrated in FIG. 1, when the width of the second stretchable wiring 30 can be regarded as being substantially constant at each position along the length direction L in the second portion 32, the width P2 of the second portion 32 of the second stretchable wiring 30 may be representatively determined at a position 2 mm away from the boundary between the first portion 31 and the second portion 32 of the second stretchable wiring 30 toward the second portion 32 side.

Further, the second stretchable wiring 30 may only have the first portion 31. In this case, the width of the second stretchable wiring 30 can be said to be smaller than the width Q of the first stretchable wiring 20 over the entire region.

The width P1 of the first portion 31 of the second stretchable wiring 30 is smaller than the width Q of the first stretchable wiring 20 in the stretchable wiring board 1. Accordingly, the durability of the first portion 31 of the second stretchable wiring 30 is reduced, possibly leading to a reduced durability in a region F1 where the first portion 31 of the second stretchable wiring 30 exists in a state where the first stretchable wiring 20 and the second stretchable wiring 30 are integrated.

In regard to this, under a state where the first stretchable wiring 20 and the second stretchable wiring 30 are integrated, as illustrated in FIG. 2, a maximum thickness R in the region F1 where the first portion 31 of the second stretchable wiring 30 exists is preferably larger than the maximum thickness in a region F2 (regions F2a and F2b to be described later) where the first portion 31 of the second stretchable wiring 30 does not exist, in the stretchable wiring board 1. Consequently, although the width P1 of the first portion 31 of the second stretchable wiring 30 is smaller than the width Q of the first stretchable wiring 20, decreases in durability in the region F1 can be reduced. Therefore, when a stress is applied to the region F1 during stretching, increases in resistance of the first stretchable wiring 20 and the second stretchable wiring 30 during stretching can be reduced.

When the second stretchable wiring 30 has the first portion 31 and the second portion 32 as illustrated in FIGS. 1, 2, 3, and 4, the range of the region F1 where decrease of durability is concerned can be prevented from being too wide due to the second portion 32. Accordingly, in the stretchable wiring board 1, increases in resistance of the first stretchable wiring 20 and the second stretchable wiring 30 during stretching can be reduced with the durability in the region F1 ensured as much as possible.

When the second stretchable wiring 30 has the first portion 31 and the second portion 32, as illustrated in FIGS. 1, 2, 3, and 4, the region F2 includes a region F2a where only the first stretchable wiring 20 exists and a region F2b where only the second stretchable wiring 30 exists.

As illustrated in FIGS. 3 and 4, the region F2a includes the portion 21b where the second stretchable wiring 30 is not overlapped in the first portion 21 of the first stretchable wiring 20, and the second portion 22 of the first stretchable wiring 20.

As illustrated in FIGS. 3 and 4, the region F2b includes the second portion 32 of the second stretchable wiring 30.

The maximum thickness in the region F2 is determined according to the regions F2a and F2b. In other words, the fact that the maximum thickness R in the region F1 is larger than the maximum thickness in the region F2 means that, the maximum thickness R in the region F1 is larger than a maximum thickness S1 in the region F2a and a maximum thickness S2 in the region F2b.

The maximum thickness S1 in the region F2a and the maximum thickness S2 in the region F2b are preferably the same, but may also be different from each other.

The maximum thickness S1 in the region F2a is determined according to the maximum thickness of the first stretchable wiring 20 in the region F2a. On the other hand, as illustrated in FIG. 2, when the thickness of the first stretchable wiring 20 can be regarded as being substantially constant at each position along the length direction L in the region F2a, the maximum thickness S1 in the region F2a may be representatively determined at a position 2 mm away from the boundary between the first portion 21 and the second portion 22 of the first stretchable wiring 20 toward the second portion 22 side.

The maximum thickness S2 in the region F2b is determined according to the maximum thickness of the second stretchable wiring 30 in the region F2b. On the other hand, as illustrated in FIG. 2, when the thickness of the second stretchable wiring 30 can be regarded as being substantially constant at each position along the length direction L in the region F2b, the maximum thickness S2 in the region F2b may be representatively determined at a position 2 mm away from the boundary between the first portion 31 and the second portion 32 of the second stretchable wiring 30 toward the second portion 32 side.

In the stretchable wiring board 1, when viewed in a direction from the region F2b toward the region F1, as illustrated in FIGS. 1 and 2, a position G where the thickness starts to increase coincides with a boundary between the region F1 and the region F2b in a state where the first stretchable wiring 20 and the second stretchable wiring 30 are integrated. More specifically, the position G where the thickness starts to increase is a boundary between the first portion 31 and the second portion 32 of the second stretchable wiring 30, and coincides with a position where the width of the second stretchable wiring 30 starts to decrease.

The position G where the thickness starts to increase may be shifted toward the side of the first stretchable wiring 20 or may be shifted toward the side opposite to the first stretchable wiring 20 with respect to the boundary between the region F1 and the region F2b, more specifically, with respect to the position where the width of the second stretchable wiring 30 starts to decrease. In particular, when the position G where the thickness starts to increase is shifted to the side opposite to the first stretchable wiring 20 with respect to the boundary between the region F1 and the region F2b, a portion having a large thickness becomes larger in the region F1, leading to an effective reduction in the durability decrease in the region F1.

The first stretchable wiring 20 and the second stretchable wiring 30 contain, for example, a metal filler and a resin.

Examples of the metal filler contained in the first stretchable wiring 20 and the second stretchable wiring 30 include a silver filler, a copper filler, and a nickel filler.

The metal filler contained in the first stretchable wiring 20 and the metal filler contained in the second stretchable wiring 30 preferably have the same type of metal, and may have different types of metal.

Examples of shapes of the metal filler contained in the first stretchable wiring 20 and the second stretchable wiring 30 include a plate shape and a spherical shape.

The metal filler contained in the first stretchable wiring 20 and the metal filler contained in the second stretchable wiring 30 preferably have the same shape, and may have different shapes.

The resin contained in the first stretchable wiring 20 and the second stretchable wiring 30 is preferably at least one elastomer resin selected from the group consisting of an acrylic resin, an epoxy resin, a urethane resin, and a silicone resin.

The resin contained in the first stretchable wiring 20 and the resin contained in the second stretchable wiring 30 are preferably the same type of resin, and may be different types of resins.

In the stretchable wiring board 1, at least one of the first stretchable wiring 20 and the second stretchable wiring 30 may be bent in a direction other than the length direction L in a region other than the range illustrated in FIGS. 1 and 2.

The stretchable wiring board 1 may further include an electrode connected to at least one of the first stretchable wiring 20 and the second stretchable wiring 30. The stretchable wiring board 1 can function as a sensor by being attached to a living body with such an electrode interposed therebetween.

The electrode is preferably a gel electrode. The stretchable wiring board 1 is easily attached to a living body via the gel electrode. The gel electrode includes, for example, conductive gel materials containing water, alcohol, a humectant, an electrolyte and others. Examples of such a gel material include a hydrogel.

Electronic components may be mounted on the stretchable wiring board 1. More specifically, at least one of the first stretchable wiring 20 and the second stretchable wiring 30 may be connected to the electronic components with respect to the stretchable wiring board 1.

Examples of the electronic components include an amplifier (operational amplifier, transistor, and the others), a diode, an integrated circuit (IC), a capacitor, a resistor, and an inductor.

The stretchable wiring board 1 is manufactured, for example, by the following method.

<First Stretchable Wiring Forming Step>

A first conductive paste containing a first metal filler and a first resin is applied in the length direction L on one main surface 11a of the stretchable substrate 10 via a screen printing method. Thereafter, the printed film of the first conductive paste is heat-treated to form the first stretchable wiring 20.

Examples of the first metal filler include a silver filler, a copper filler, and a nickel filler.

Examples of shapes of the first metal filler include a plate shape and a spherical shape.

The first resin is preferably at least one elastomer resin selected from the group consisting of an acrylic resin, an epoxy resin, a urethane resin, and a silicone resin.

The first conductive paste may further contain a solvent. Examples of such solvents include diethylene glycol monoethyl ether acetate.

<Second Stretchable Wiring Forming Step>

A second conductive paste including a second metal filler and a second resin is applied in the length direction L on one main surface 11a of the stretchable substrate 10 via a screen printing method, so as to overlap on top of the first stretchable wiring 20 on the one end portion 30a side. At such a time, the second conductive paste is applied by adjusting the specifications including a pattern and a mesh of the screen printing plate, so that the width is smaller than that of the first stretchable wiring 20 at least in a portion overlapping with the first stretchable wiring 20. Accordingly, regardless of whether the printing bleedings of the second conductive paste occur due to the step of the first stretchable wiring 20, the width is made smaller than that of the first stretchable wiring at least in a portion overlapping with the first stretchable wiring 20 in the second conductive paste after applying the second conductive paste. Thereafter, the printed film of the second conductive paste is heat-treated to form the second stretchable wiring 30.

The second stretchable wiring 30 formed in this way has a first portion 31 located on the one end portion 30a side. The first portion 31 of the second stretchable wiring 30 has at least a region E1 where the first stretchable wiring 20 and the second stretchable wiring 30 overlap. Further, the width P1 of the first portion 31 of the second stretchable wiring 30 is smaller than the width Q of the first stretchable wiring 20.

Examples of the second metal filler include a silver filler, a copper filler, and a nickel filler.

The first metal filler and the second metal filler preferably have the same type of metal, and may have different types of metals.

Examples of shapes of the second metal filler include a plate shape and a spherical shape.

The first metal filler and the second metal filler preferably have the same shape, and may have different shapes.

The second resin is preferably at least one elastomer resin selected from the group consisting of an acrylic resin, an epoxy resin, a urethane resin, and a silicone resin.

The first resin and the second resin are preferably the same type of resin, and may be different types of resins.

The second conductive paste may further contain a solvent. Examples of such solvents include diethylene glycol monoethyl ether acetate.

When the first conductive paste and the second conductive paste contain a solvent, the solvent contained in the first conductive paste and the solvent contained in the second conductive paste are preferably the same type of solvent, and may be different types of solvents.

In the method described above, the first stretchable wiring 20 is formed by sequentially performing the printing with the first conductive paste and the heat treatment for the printed film of the first conductive paste, and then the second stretchable wiring 30 is formed by sequentially performing the printing with the second conductive paste and the heat treatment for the printed film of the second conductive paste. In other words, the first stretchable wiring 20 and the second stretchable wiring 30 are formed at different timings in the method above.

On the other hand, different from the method above, the first stretchable wiring 20 and the second stretchable wiring 30 may be formed at the same time by sequentially performing the printings with the first conductive paste and printing with the second conductive paste, and then performing heat treatments for the printed films of the first conductive paste and the second conductive paste.

In this way, the stretchable wiring board 1 is manufactured.

The devices with an adhesive patch for living bodies of the present invention include the stretchable wiring board of the present invention. Examples of the devices with an adhesive patch for living bodies of the present invention include a device with an adhesive patch for living bodies having the stretchable wiring board 1 illustrated in, for example, FIG. 1. According to such devices with an adhesive patch for living bodies, biological information can be acquired and analyzed by attaching the stretchable wiring board 1 to a living body.

DESCRIPTION OF REFERENCE SYMBOLS

1: Stretchable wiring board
10: Stretchable substrate
11a: Main surface of stretchable substrate
20: First stretchable wiring
20a: One end portion of first stretchable wiring
21: First portion of first stretchable wiring
21a: Portion overlapping with second stretchable wiring in first portion of first stretchable wiring
21b: Portion not overlapping with second stretchable wiring in first portion of first stretchable wiring
22: Second portion of first stretchable wiring
30: Second stretchable wiring
30a: One end portion of second stretchable wiring
31: First portion of second stretchable wiring
32: Second portion of second stretchable wiring
E1: Region where first stretchable wiring and second stretchable wiring overlap
E2: Region where first stretchable wiring and second stretchable wiring do not overlap
F1: Region where first portion of second stretchable wiring exists
F2: Region where first portion of second stretchable wiring does not exist
F2a: Region where only first stretchable wiring exists in region where first portion of second stretchable wiring does not exist
F2b: Region where only second stretchable wiring exists in region where first portion of second stretchable wiring does not exist
G: Position where thickness starts to increase
L: Length direction
P1: Width of first portion of second stretchable wiring
P1': Width determined at center position in length direction in first portion of second stretchable wiring
P2: Width of second portion of second stretchable wiring Q, Q': Width of first stretchable wiring
R: Maximum thickness in region where first portion of second stretchable wiring exists
S1: Maximum thickness in region where only first stretchable wiring exists in region where first portion of second stretchable wiring does not exist
S2: Maximum thickness in region where only second stretchable wiring exists in region where first portion of second stretchable wiring does not exist
T: Thickness direction
W: Width direction

The invention claimed is:

1. A stretchable wiring board comprising:
a stretchable substrate;
a first stretchable wiring extending in a length direction on a main surface side of the stretchable substrate, the first stretchable wiring having a first extending portion and a first terminated end portion connected to the first extending portion; and
a second stretchable wiring extending in the length direction on the main surface side of the stretchable substrate, the second stretchable wiring having a second extending portion and a second terminated end portion connected to the second extending portion, the second terminated end portion overlapping on top of the first terminated end portion of the first stretchable wiring and not the first extending portion of the first stretchable wiring, and a width of the second terminated end portion of the second stretchable wiring in a width direction orthogonal to the length direction is smaller than a width of the first terminated end portion of the first stretchable wiring.

2. The stretchable wiring board according to claim 1, wherein a maximum thickness in a thickness direction orthogonal to the length direction and the width direction in a first region where the second terminated end portion of the second stretchable wiring exists is larger than a maximum thickness in a second region where the second terminated end portion of the second stretchable wiring does not exist.

3. A stretchable wiring board comprising:
a stretchable substrate;
a first stretchable wiring extending in a length direction on a main surface side of the stretchable substrate; and
a second stretchable wiring extending in the length direction on the main surface side of the stretchable substrate, the second stretchable wiring having a first portion with a first region overlapping on top of the first stretchable wiring on an end portion side of the first stretchable wiring, and a width of the first portion of the second stretchable wiring in a width direction orthogonal to the length direction is smaller than a width of the first stretchable wiring,
wherein the first portion of the second stretchable wiring exists across a second region where the first stretchable wiring and the second stretchable wiring overlap and a third region where the first stretchable wiring and the second stretchable wiring do not overlap, and
wherein a length of the first portion in the third region where the first stretchable wiring and the second stretchable wiring do not overlap is 100 μm to 300 μm.

4. The stretchable wiring board according to claim 1, wherein a width of the second extending portion of the second stretchable wiring is larger than the width of the second terminated end portion of the second stretchable wiring.

5. A stretchable wiring board comprising:
a stretchable substrate;
a first stretchable wiring extending in a length direction on a main surface side of the stretchable substrate; and
a second stretchable wiring extending in the length direction on the main surface side of the stretchable substrate, the second stretchable wiring having a first portion with a first region overlapping on top of the first stretchable wiring on an end portion side of the first stretchable wiring, and a width of the first portion of the second stretchable wiring in a width direction orthogonal to the length direction is smaller than a width of the first stretchable wiring,
wherein
the second stretchable wiring includes the first portion and a second portion adjacent to the first portion in the length direction, and
a width of the second portion of the second stretchable wiring is larger than the width of the first portion of the second stretchable wiring, and
wherein a difference between the width of the first portion of the second stretchable wiring at a center position in the length direction in the first portion of the second stretchable wiring and the width of the second portion of the second stretchable wiring is 30 μm or more.

6. A stretchable wiring board comprising:
a stretchable substrate;
a first stretchable wiring extending in a length direction on a main surface side of the stretchable substrate; and
a second stretchable wiring extending in the length direction on the main surface side of the stretchable substrate, the second stretchable wiring having a first portion with a first region overlapping on top of the first stretchable wiring on an end portion side of the first stretchable wiring, and a width of the first portion of the second stretchable wiring in a width direction orthogonal to the length direction is smaller than a width of the first stretchable wiring,
wherein
the second stretchable wiring includes the first portion and a second portion adjacent to the first portion in the length direction, and
a width of the second portion of the second stretchable wiring is larger than the width of the first portion of the second stretchable wiring, and
wherein the width of the second portion of the second stretchable wiring is the same as the width of the first stretchable wiring.

7. A stretchable wiring board comprising:
a stretchable substrate;
a first stretchable wiring extending in a length direction on a main surface side of the stretchable substrate; and
a second stretchable wiring extending in the length direction on the main surface side of the stretchable substrate, the second stretchable wiring having a first portion with a first region overlapping on top of the first stretchable wiring on an end portion side of the first stretchable wiring, and a width of the first portion of the second stretchable wiring in a width direction orthogonal to the length direction is smaller than a width of the first stretchable wiring,
wherein a difference between the width of the first portion of the second stretchable wiring at a center position in the length direction in the first portion of the second stretchable wiring and a width of the first stretchable wiring is 30 μm or more.

8. A stretchable wiring board comprising:
a stretchable substrate;
a first stretchable wiring extending in a length direction on a main surface side of the stretchable substrate; and
a second stretchable wiring extending in the length direction on the main surface side of the stretchable substrate, the second stretchable wiring having a first portion with a first region overlapping on top of the first stretchable wiring on an end portion side of the first stretchable wiring, and a width of the first portion of the second stretchable wiring in a width direction orthogonal to the length direction is smaller than a width of the first stretchable wiring,
wherein a difference between the width of the first portion of the second stretchable wiring at a center position in the length direction in the first portion of the second stretchable wiring and a width of the first stretchable wiring is half or less of the width of the first stretchable wiring.

9. A device with an adhesive patch for living bodies, the device comprising the stretchable wiring board according to claim 1.

\* \* \* \* \*